US008875372B2

(12) United States Patent
McHugo (10) Patent No.: US 8,875,372 B2
(45) Date of Patent: Nov. 4, 2014

(54) BRAIDED HELICAL WIRE STENT

(75) Inventor: Vincent McHugo, County Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 201 days.

(21) Appl. No.: 13/595,151

(22) Filed: Aug. 27, 2012

(65) Prior Publication Data

US 2013/0060323 A1    Mar. 7, 2013

Related U.S. Application Data

(60) Provisional application No. 61/530,156, filed on Sep. 1, 2011.

(51) Int. Cl.
| | | |
|---|---|---|
| *B23P 11/00* | (2006.01) | |
| *A61F 2/90* | (2013.01) | |
| *D04C 3/48* | (2006.01) | |
| *D04C 1/06* | (2006.01) | |
| *D04C 7/00* | (2006.01) | |

(52) U.S. Cl.
CPC ... *D04C 7/00* (2013.01); *A61F 2/90* (2013.01); *D10B 2509/06* (2013.01); *D04C 3/48* (2013.01); *D04C 1/06* (2013.01); *A61F 2240/001* (2013.01)
USPC .......................................................... 29/439

(58) Field of Classification Search
USPC .......... 29/439, 433, 428, 469; 623/1.18, 1.11, 623/1.22, 1, 53, 1.46
See application file for complete search history.

(56) References Cited

U.S. PATENT DOCUMENTS

| | | |
|---|---|---|
| 6,007,574 A | 12/1999 | Pulnev et al. |
| 6,309,415 B1 | 10/2001 | Pulnev et al. |
| 6,641,608 B1 | 11/2003 | Pulnev |
| 7,927,366 B2 | 4/2011 | Pulnev et al. |
| 2004/0167611 A1 | 8/2004 | Pulnev et al. |
| 2007/0073386 A1 | 3/2007 | Pulnev et al. |
| 2007/0078508 A1 | 4/2007 | Pulnev et al. |
| 2008/0288054 A1 | 11/2008 | Pulnev et al. |
| 2008/0312734 A1 | 12/2008 | Pulnev et al. |
| 2009/0210048 A1 | 8/2009 | Amplatz et al. |
| 2010/0191319 A1 | 7/2010 | Lilburn et al. |
| 2010/0211162 A1 | 8/2010 | Pulnev et al. |
| 2010/0241218 A1 | 9/2010 | Bruszewski et al. |
| 2011/0166639 A1 | 7/2011 | Pulnev et al. |
| 2011/0166643 A1 | 7/2011 | Pulnev et al. |
| 2012/0186420 A1 | 7/2012 | Lilburn et al. |

FOREIGN PATENT DOCUMENTS

| | | |
|---|---|---|
| WO | WO 2009/105395 A2 | 8/2009 |
| WO | WO 2010/085794 A2 | 7/2010 |
| WO | WO 2010/111011 A1 | 9/2010 |

OTHER PUBLICATIONS

Notification of Transmittal of the International Search Report and the Written Opinion of the International Searching Authority, or the Declaration, dated Apr. 4, 2013, from corresponding application PCT/US2012/052461, 5p.

*Primary Examiner* — John C Hong
(74) *Attorney, Agent, or Firm* — Brinks Gilson & Lione (57) ABSTRACT

Exemplary non-woven helical stents are described that are efficient to fabricate in terms of labor and resources by being able to be manufactured by hand or machine while providing mechanical stability equivalent or close thereto of known braided or woven stents.

14 Claims, 6 Drawing Sheets

BRAIDED HELICAL WIRE STENT

RELATED APPLICATION

This application claims the benefit of priority from U.S. Provisional Application No. 61/530,156, filed Sep. 1, 2011, and titled "Braided Helical Wire Stent", the contents of which is incorporated herein by reference.

TECHNICAL FIELD

The present invention relates to medical devices and more specifically, stents.

BACKGROUND

Stents are tubular shaped medical devices commonly used to maintain patency of diseased body vessels. Stents may be implanted to treat blockages, occlusions, narrowing ailments, and other problems that can restrict flow through a vessel. Stents can be implanted, for example, in the coronary and peripheral arteries to maintain blood flow, in the ureters and biliary tract to provide drainage, and in the esophagus to palliate dysphagia.

Stents are often delivered in a radially compressed state via a minimally invasive procedure and thereafter expanded to contact and support the inner wall of the targeted vessel. Both self-expanding and balloon-expandable stents are amenable to radial compression and subsequent expansion at the treatment site. Balloon-expandable stents expand in response to the inflation of a balloon, whereas self-expanding stents deploy automatically when released from a delivery device.

Self-expanding stents are useful for a variety of procedures requiring the patency of a bodily pathway. Such stents are generally biased to expand, such that when deployed, they assume an open position, pushing outward and into the surrounding area into which deployed. The radial expansion creates a pathway in a once occluded area.

One type of self-expanding stent includes single wire stents designed for implantation in the gastrointestinal system (e.g., esphophagus, colon, biliary tree, etc). These braided stent structures are flexible enough to accommodate typical movements of such bodily organs, but they simultaneously provide sufficient rigidity to maintain patency of the vessel. A single wire stent typically includes a helical weave or braid configuration where the wires of opposing helicals pass in an alternating fashion under and over each other. This interweaved pattern gives stability to the stent structure. However, the current manufacturing process for these types of single wire woven stents is extremely labor intensive and expensive, as they are typically hand woven with the assistance of a mandrel. For larger stents, it can take up to sixteen hours for a highly skilled artisan to manufacture the tubular frame utilizing a wire measuring about eight meters in length. This long wire is laboriously threaded together to form the final stent weave pattern. Automated machine processes are currently unavailable.

BRIEF SUMMARY

In a first aspect, a stent is provided, the stent including a wire having a wire first portion and a wire second portion; wherein the wire first portion is configured into a first elongated tubular body having a first helical pattern; wherein the wire second portion is configured into a second elongated tubular body having a second helical pattern having a pitch about opposite a pitch of the first helical pattern; wherein the wire first portion and the wire second portion are braided together forming a stent wall having an elongated tubular braided helical pattern.

In a second aspect, a method of forming a stent is provided, including providing a wire having a wire first portion and a wire second portion; wrapping the wire first portion around a mandrel thereby forming a first elongated tubular body having a first helical pattern; wrapping the wire second portion around the mandrel thereby forming a second elongated tubular body around the first elongated tubular body, wherein the second elongated tubular body has a second helical pattern having a pitch about opposite a pitch of the first helical pattern; wherein the first elongated tubular body and the second elongated tubular body together form a third elongated tubular body having a double helical pattern; heat-setting the third elongated tubular body such that it is biased to assume an expanded state from a compressed state; unwinding the wire second portion from the third elongated tubular body; unwinding the wire first portion from the third elongated tubular body; and braiding the wire first portion and the wire second portion forming a stent wall having an elongated tubular body having a braided helical pattern.

In a third aspect, a method of forming a stent is provided, including providing a wire having a wire first portion and a wire second portion; loading the wire first portion and the wire second portion onto a mandrel tooling to form loops of wire; forming a stent wall by braiding the loops into an elongated tubular body having a braided helical pattern; heat-setting the stent wall such that it is biased to assume an expanded state from a compressed state.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

DETAILED DESCRIPTION OF PRESENTLY PREFERRED EMBODIMENTS

The exemplary embodiments illustrated herein provide the discovery of exemplary apparatuses and methods for stents that are not laborious to fabricate and that may be fabricated quickly, efficiently, and at decreased cost using a machine or human being. The present invention is not limited to those embodiments described herein, but rather, the disclosure includes all equivalents including those of different shapes, sizes, and configurations, including but not limited to, other types of stents. For example, the principles herein can be applied to other types of stents, including but not limited to, self-expanding metal stents, balloon expandable stent, woven wire stents, and the EVOLUTION® (Wilson-Cook Medical Inc.). The devices and methods can be used in any field benefiting from a stent, including but not limited to, the biliary, colonic, esophageal, vascular, and trachea regions. Additionally, the devices and methods are not limited to being used with a human being, others are contemplated, including but not limited to, animals.

A more detailed description of the embodiments will now be given with reference to FIGS. 1-2E. Throughout the disclosure, like reference numerals and letters refer to like elements. The present disclosure is not limited to the embodiments illustrated; to the contrary, the present disclosure specifically contemplates other embodiments not illustrated but intended to be included in the claims.

Figure 1:
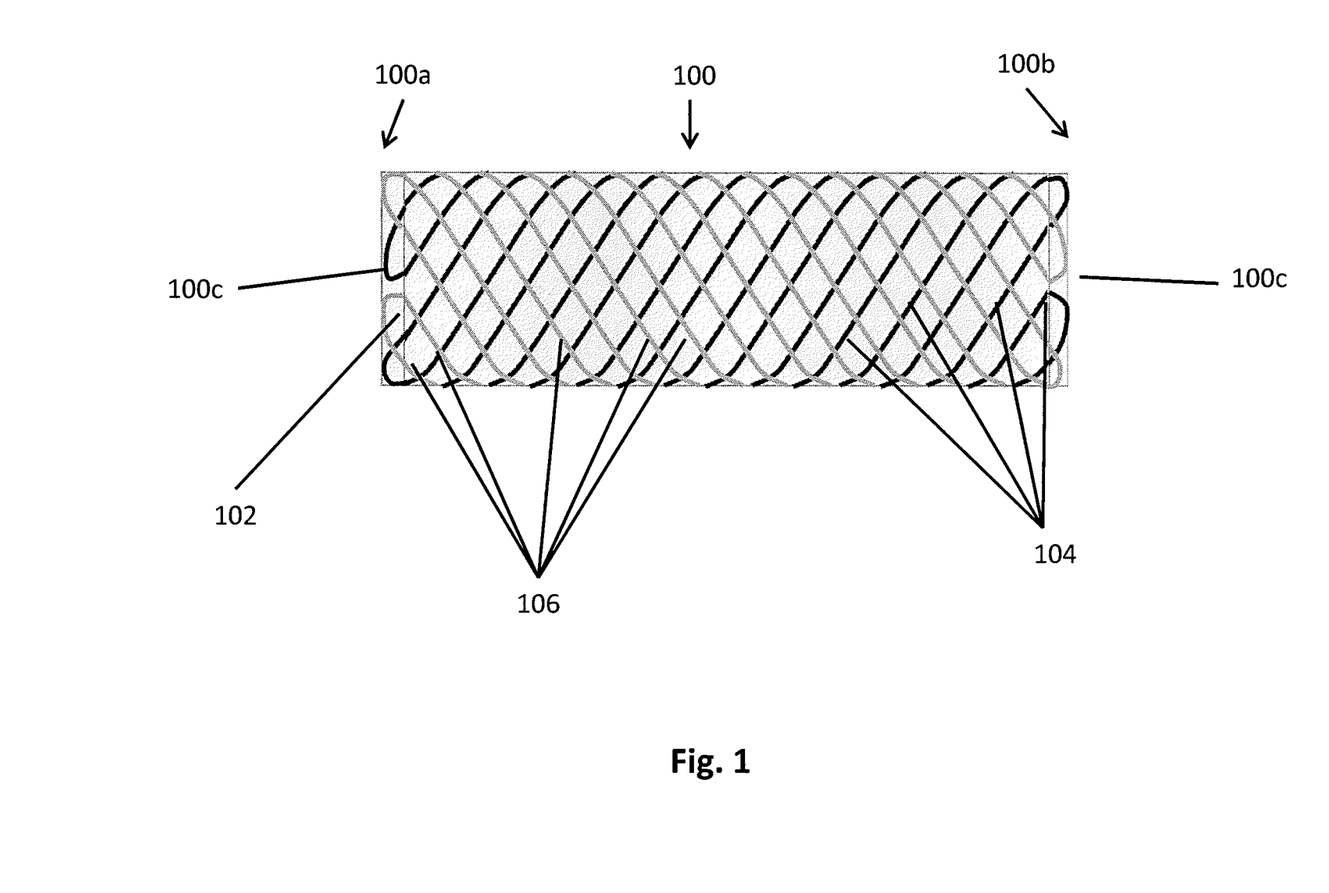
FIG. 1 illustrates a stent manufactured by an efficient means.

FIG. 1 illustrates stent 100 manufactured by an efficient means. Stent 100 has proximal portion 100a, distal portion 100b, and lumen 100c extending throughout. Stent 100 is constructed having a single braided (platted) helical wire pattern using a single wire comprising wire first portion 104 and wire second portion 106 to form the stent wall.

The filament or wire used to construct stent 100, for example comprising wire first portion 104 and wire second portion 106, may be of various cross-sectional shapes and sizes. For example, wire first portion 104 and wire second portion 106 may be flat in shape or may have a circular-shaped cross-section. Wire first portion 104 and wire second portion 106 may have any suitable diameter, such as for example, from about 0.10 mm to about 0.30 mm. Other dimensions and configurations are contemplated.

Expandable stents illustrated and equivalents thereto may be formed from a variety of biocompatible materials. For example, wire first portion 104 and wire second portion 106 preferably comprises one or more elastically deformable materials such as shape memory alloys (e.g., stainless steel, nitinol, and the like), although other materials are contemplated. For example, wire first portion 104 and wire second portion 106 may also be made from or comprise any suitable biocompatible material(s). For example, stents illustrated and equivalents thereto may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used in part to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Current double helical wire stents may use a single wire that can be upwards of eight meters long for a single stent, and it must be laboriously threaded together to form the final stent weave pattern.

Automated machines for forming single wire stents are unavailable. Automated machines may be used to manufacture helical wire stents. However, they require the use of multiple wires, thereby necessitating that the wires be welded together at each end of the stent. This reduces stent stability and durability.

Through the use of a machine or being constructed by hand, stent 100 has, inter alia, a benefit of being constructed more quickly and efficiently than compared to the labor intensive process normally involved in human construction of a double helical stent. For example, it is contemplated that a human or machine may be able to construct stent 100 in less than 1.25 hours as opposed to a similarly-sized double helical stent, which may take up to sixteen hours for a human to manufacture by hand depending upon the size of the stent.

Stents illustrated and equivalents thereto may include one or more purse strings, such as loops, lassos, or sutures on the stent structure to facilitate repositioning or removal of the stent during or after implantation. For example, stents illustrated and equivalents thereto may include one or more loops at or near the proximal end and/or distal end of the stent, as well as one or more sutures disposed through the lumen of the stent. The loop material may circumscribe the end and in some embodiments may be wound through the absolute end cells to affix the loop to the stent. The loop may comprise any appropriate biocompatible materials, such as for example, suture materials or other polymeric or metallic materials such as polyethylene, ultra-high molecular weight polyethylene, polyester, nylon, stainless steel, nitinol, or the like. Optionally, the lasso may be covered with a material, such as polytetrafluoroethylene, to reduce frictional interactions of the lasso with surrounding tissue. The purse string may be configured to compress the stent when an axial force is applied to it.

Stents illustrated and equivalents thereto may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary or desired. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., EVOLUTION® Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

Alternatively, it is also contemplated that stents illustrated and equivalents thereto may be configured for delivery and placement using a system such as that described in U.S. patent application Ser. No. 13/015,764, entitled "Mechanically Expandable Delivery and Dilation Systems," filed Jan. 28, 2011, and incorporated in its entirety herein by reference, describing, for example, a stent delivery system that includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration, a proximal constraining member and a distal constraining member releasably connected to the stent and having a first position and a second position are also included, wherein the proximal constraining member and the distal constraining member cooperatively apply a longitudinal tensile force to at least a portion of the stent in the constrained configuration with the proximal and distal constraining members each in the first position.

Stents illustrated and equivalents thereto may be fabricated to any suitable dimensions. Stents illustrated and equivalents thereto having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter.

A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

Stents illustrated and equivalents thereto may have any suitable helical pattern or angle. The radial force of the stent may be controlled by adjusting the angle accordingly. Stents with higher angles typically exert greater radial force and exhibit greater foreshortening during expansion from a compressed state. Stents with lower angles typically exert lower radial force and experience less foreshortening upon expansion. In some instances, the angle can be lowered because the membrane covering typically adds rigidity to the stent structure. In addition to adjusting the angle, the radial force of the stent can be adjusted through selection of particular filament materials, as well as the shape and size of the filaments or wires forming the stent structure.

Stents illustrated and equivalents thereto may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of wire first portion 104 and wire second portion 106. In some embodiments, a stent may include four radiopaque markers with two markers affixed to a first flange and two to a second flange. Optionally, radiopacity can be added to a stent through covering (also referred to as coating) processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate. Additional methods are contemplated, including but not limited to, use of a nitinol wire with a platinum core, such as the DFT® wire available from Fort Wayne Metals, Fort Wayne, Ind.

Stents illustrated and equivalents thereto may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract. One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization as well as working channels through which devices and instruments may be delivered to the site of implantation. A fluoroscope also provides visualization of the patient anatomy to aid in placement of an implantable device, particularly in the gastrointestinal system. Additionally, the stent may be post-dilated with a balloon or other means.

Although covering 102 is illustrated as being a silicone elastomer, which is desired given its ability to stretch generally 500-700% without being compromised and such, is useful in stent applications, other covering materials are contemplated, including but not limited to, polyethylene (the fibers of which could be applied in layers at the same pitch of wire first portion 104 and wire second portion 106 to help close the gaps and provide a seal-like covering (but an air or water-tight seal need not be achieved)), TYVEK® (DuPont) (or other like materials) which are contemplated as being sandwiched between wire first portion 104 and wire second portion 106, as well as other non-woven materials. Indeed it is also completed that other fabric layers with filaments running in one direction that matches the pitch of one or more of wire first portion 104 and wire second portion 106 could be used as a covering. As such, the covering could be made up of several layers with the filaments running in one direction with a pitch similar to one or more of wire first portion 104 and wire second portion 106 with the direction of the helical pattern alternated between layers. It is contemplated that such fabric layer may be bonded to one or more of first portion 104 and wire second portion 106.

Indeed, in some embodiments, the covering membrane may cover over the entire stent framework from the proximal end to the distal end. In other embodiments, the stent may have a covering over a central portion of the structure and one or more uncovered ends or flanges. Moreover, a membrane covering may comprise any suitable biocompatible material. Preferably, the membrane covering is an elastic or flexible material that can adapt to radial compression of a stent prior to delivery, as well as foreshortening of a stent during expansion from a compressed state. Suitable membrane materials include, for example, silicones (e.g. polysiloxanes and substituted polysiloxanes), polyurethanes, thermoplastic elastomers, polyolefin elastomers, polyethylene, polytetrafluoroethylene, nylon, and combinations thereof. In some embodiments, where the stent will be implanted at or near an acidic environment (e.g., being exposed to gastric fluids), preferably the membrane covering is resistant to acid degradation.

Stents illustrated and equivalents thereto may include a membrane covering applied by any suitable method as is known in the art. For example, the membrane may be applied by spraying, dipping, painting, brushing, or padding. Generally, the membrane covering has a thickness ranging from about 0.0025 mm to about 2.5 mm. The thickness of the membrane may be selected, for example, by controlling the number of dips or passes made during the application process.

In some embodiments, a stent may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent. In such configuration, the release of the bioactive agent may be dependent on factors including composition, structure and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a stent having multiple coverings. Different bioactive agents may be present in the different layers.

A variety of bioactive agents may be applied to the stent in accordance with the intended use. A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known.

Prior to applying a membrane covering, and/or a bioactive agent, a stent may be polished, cleaned, and/or primed as is known in the art. A stent may be polished, for example, with an abrasive or by electropolishing. A stent may be cleaned by inserting the stent into various solvents, degreasers and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure.

In addition the use of a covering, prevention or the limiting of motion between wire first portion 104 and wire second portion 106 could also be achieved or aided by placing a bump feature onto one or more of wire first portion 104 and wire second portion 106 at the places where wire first portion 104 and wire second portion 106 cross each other, such as by roughening the surface of wire first portion 104 or wire second portion 106 at the cross-over points such as where wire second portion 106 crosses over wire first portion 104 (or visa-versa) to help wire first portion 104 and wire second portion 106 engage each other and prevent wire migration by way of increased friction therebetween. Roughening of the surface of one or more of wire first portion 104 and wire second portion 106 or portions thereof can be achieved by means of, including but not limited to, filing and sand blasting. A weld may also be placed at one or more cross over points as a securing means.

Although the aforementioned illustrated embodiments depict a stent having a substantially uniform diameter on the longitudinal axis, other stent configurations are possible. A stent may include a central body portion and one or more uniform flanges, or it may have two asymmetrically shaped flanges. A stent may include a uniform diameter along the length of stent but include a slightly flared proximal end and/or distal end. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the proximal and distal ends engage healthy tissue adjacent the diseased area.

FIGS. 2A-2E illustrate a method for manufacturing a modified stent, such as that illustrated in FIG. 1. The entire method or any portion thereof can be performed by a machine to, for example, improve manufacturing efficiency. Performance of the method is not limited to a machine; others are contemplated, including but not limited to, performance or partial performance being conducted by a human being. It is contemplated that the wire looping process could be completed in about ten minutes and the braiding process could take about one hour, depending upon the size of the stent.

Figure 2A:
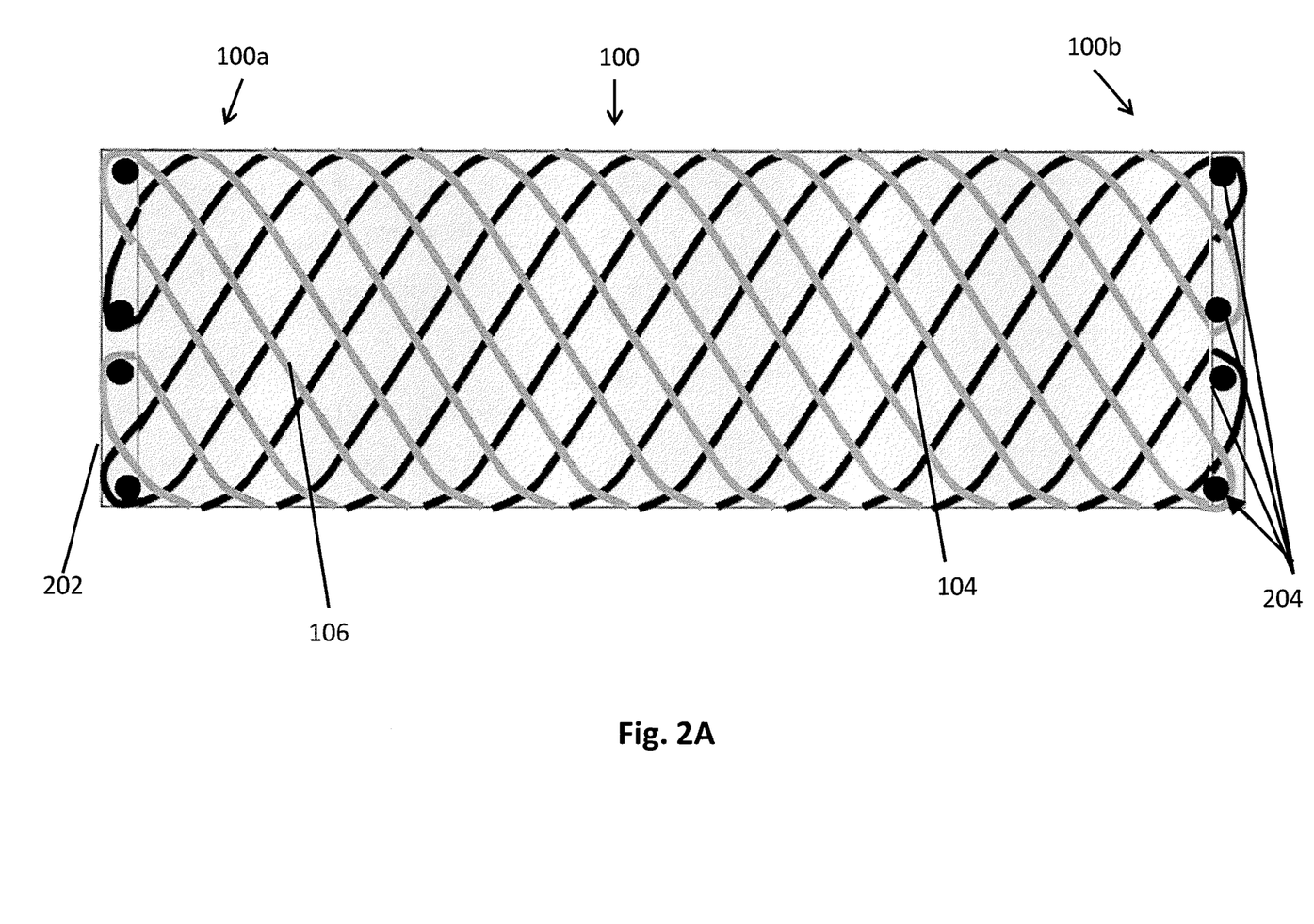
FIGS. 2A-2E illustrate a method for manufacturing a stent, such as that illustrated in FIG. 1.
Figure 2B:
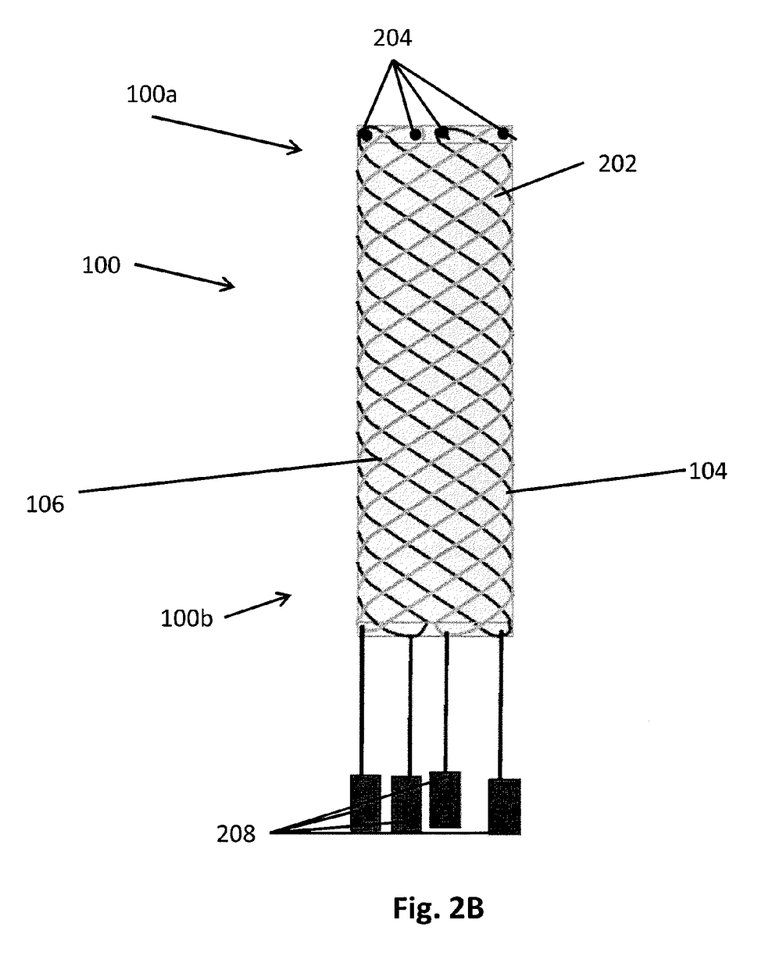
Figure 2C:
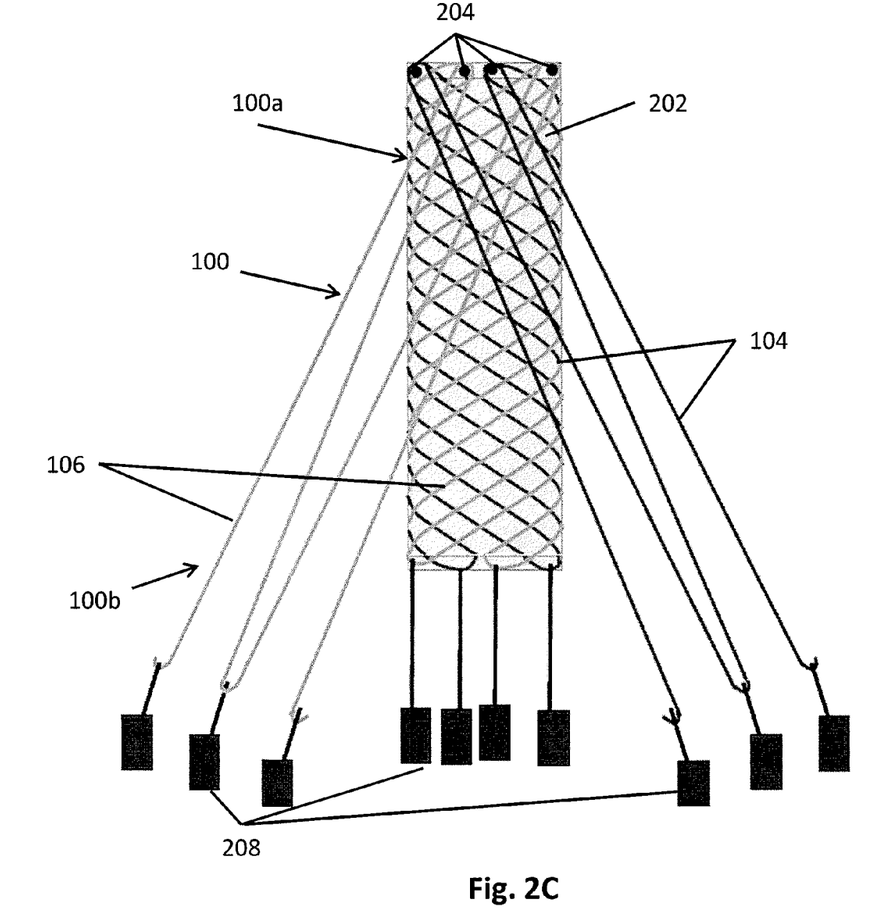
Figure 2D:
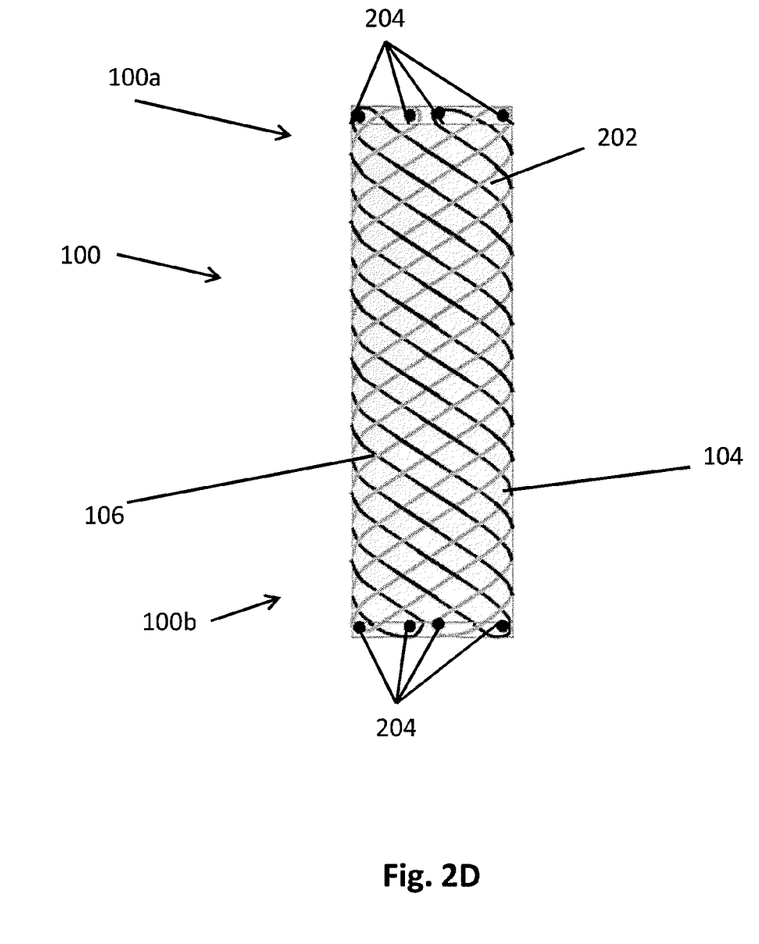
Figure 2E:
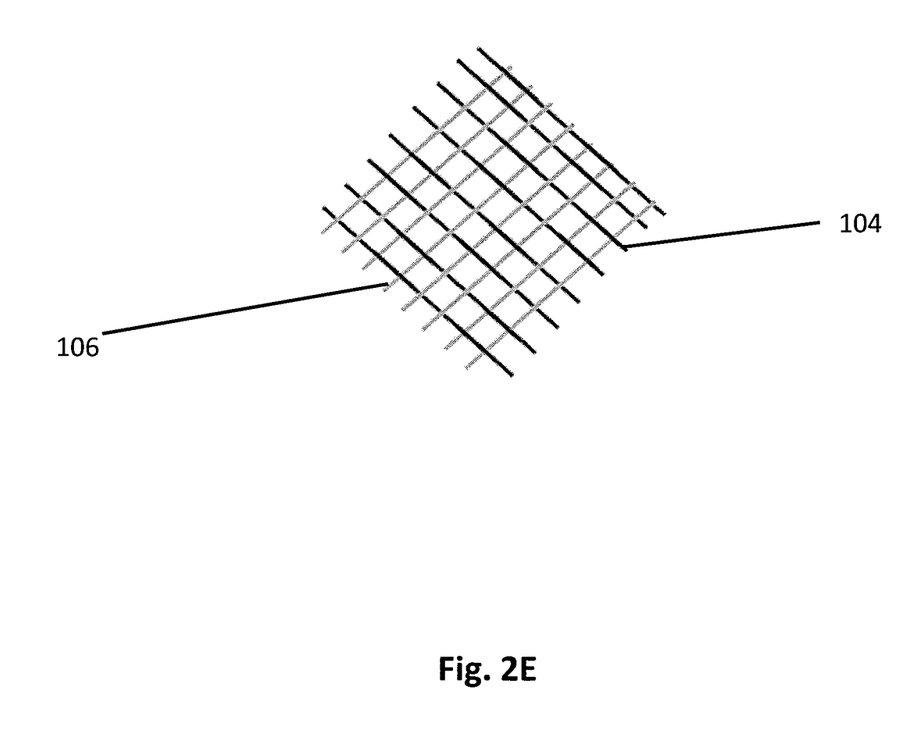

Wire first portion 104 and wire second portion 106 are not woven, but instead, are formed into a double helical pattern and then braided together forming the braided helical wire pattern illustrated in FIGS. 1 and 2E. In other words, each portion of the wire is heat set into a helical orientation, and then each of those portions is then braided together and heat-set to form a stent wall having a braided helical pattern.

Referring to FIG. 2A, a single wire comprising wire first portion 104 and wire second portion 106, preferably made from nitinol (although other materials are contemplated as illustrated above), is looped over mandrel 202 and around pins 204 connected to mandrel 202, to form a helical pattern wherein wire first portion 104 is wound around mandrel first, and wire second portion 106 is wound over wire first portion 104, forming a double helical pattern. The double helical wire pattern is then heat-set on mandrel 202 such that wire first portion 104 and wire second portion 106 are biased to assume the expanded double helical pattern. As is illustrated in FIG. 2A, first wire portion 104 is wrapped having a first helical pattern, and second wire portion 106 is then wrapped over first wire portion 104 such that second wire portion 106 has a helical pattern having a pitch about opposite of the helical pitch of first wire portion 104. Because wire 104, 106 is heat-set into the double helical orientation, wire 104, 106 is biased to assume a double helical orientation.

Referring to FIG. 2B, stent 100 is then vertically supported and weights 208 are applied to distal portion 100b of wire first portion 104 and wire second portion 106 loops. It is contemplated that tension could be applied in different ways.

Referring to FIG. 2C, loops of wire first portion 104 and wire second portion 106 are then unwound from mandrel 202 and pins 204, whereby wire second portion 106 is unwound first, and wire first portion 104 is unwound thereafter. However, because wire 104, 106 had been heat-set into a double helical orientation as illustrated above, wire 104, 106 is biased to resume its double helical orientation.

Referring to FIG. 2D, loops of wire first portion 104 and wire second portion 106 are then braided back over and under each other on mandrel 202 and around pins 204 such that a braided helical pattern is formed. In other words, the double helical wire portions are braided such that they together form a braided helical pattern forming a stent wall. Stent 100 is then heat-set into its configuration, for a second time, such that wire first portion 104 and wire second portion 106 are biased to assume an expanded braided helical wire configuration. An optional silicone membrane or other coating, such as that illustrated in FIG. 1, may be applied.

FIG. 2E, illustrates the resulting double wire over and under pattern of stent 100, illustrated in FIG. 2D.

Alternatively, different braiding patterns are contemplated, including but not limited to, those using a single wire or multiple wires, having similar or different patterns, including but not limited to, those having parallel wire orientations.

It is contemplated that construction of stent 100 is also possible without initially forming it into a double helical pattern, but instead, stent 100 may be manufactured using a single heat-set process by loading wire first portion 104 and wire second portion 106 onto mandrel tooling to form loops of wire and then braiding such loops into the final pattern to be heat-set shaped. Such a process would lend well for machine automation and would further reduce cost while still providing a durable stent like stent 100 having, inter alia, improved stability and reliability.

From the foregoing, the discovery of a non-woven helical stent that is efficient to fabricate by being able to be manufactured by hand or machine while providing mechanical stability equivalent or close thereto of known braided or woven stents will benefit patients both in having an improved means for treating ailments as well as likely reducing the cost of treatment. It can be seen that the stents illustrated and equivalents thereof as well as the methods of manufacturer may utilize machines or other resources, such as human beings, thereby reducing the time, labor, and resources required to manufacturer a stent. Indeed, the discovery is not limited to the embodiments illustrated herein, and the principles and methods illustrated herein can be applied and configured to any stent and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A method of forming a stent comprising the steps of:
   providing a wire comprising a wire first portion and a wire second portion;
   wrapping the wire first portion around a mandrel thereby forming a first elongated tubular body comprising a first helical pattern;
   wrapping the wire second portion around the mandrel thereby forming a second elongated tubular body around the first elongated tubular body, wherein the second elongated tubular body comprises a second helical pattern comprising a pitch about opposite a pitch of the first helical pattern; wherein the first elongated tubular body and the second elongated tubular body together form a third elongated tubular body comprising a double helical pattern;
   heat-setting the third elongated tubular body such that it is biased to assume an expanded state from a compressed state;
   unwinding the wire second portion from the third elongated tubular body;
   unwinding the wire first portion from the third elongated tubular body;
   braiding the wire first portion and the wire second portion forming a stent wall comprising an elongated tubular body comprising a braided helical pattern; and
   heat-setting the stent wall such that it is biased to assume an expanded braided helical wire configuration.

2. The method of claim 1, wherein the step of braiding the wire first portion and the wire second portion comprises braiding the wire first portion and the wire second portion over and under each other.

3. The method of claim 1, further comprising step of applying a plurality of weights to a plurality of loops of the third elongated tubular body.

4. The method of claim 1, further comprising the step of affixing a suture to the stent wall.

5. The method of claim 1, wherein the wire comprises a shape-memory alloy.

6. The method of claim 1, further comprising the step of affixing a radiopaque marker to the stent wall.

7. The method of claim 1, wherein the step of wrapping the wire first portion around a mandrel is performed at least in part by a machine.

8. The method of claim 1, wherein the step of wrapping the wire second portion around the mandrel is performed at least in part by a machine.

9. The method of claim 1, wherein the steps of braiding the wire first portion and braiding the wire second portion are each performed at least in part by a machine.

10. A method of forming a stent comprising the steps of:
    providing a wire comprising a wire first portion and a wire second portion;
    loading the wire first portion and the wire second portion onto a mandrel tooling to form loops of wire, wherein the loops of the wire second portion are disposed on top of the loops of the wire first portion in an non-woven manner;
    removing the loops of the wire first portion and the loops of the wire second portion from the mandrel tooling;
    forming a stent wall by braiding the loops of the wire first portion and the loops of the wire second portion into an elongated tubular body comprising a braided helical pattern; and
    heat-setting the stent wall such that it is biased to assume an expanded state from a compressed state.

11. The method of claim 10, further comprising the step of affixing a suture to the stent wall.

12. The method of claim 10, wherein the wire comprises a shape-memory alloy.

13. The method of claim 10, further comprising the step of affixing a radiopaque marker to the stent wall.

14. The method of claim 10, wherein the step of forming the stent wall is performed at least in part by a machine.

* * * * *